US011406315B2

(12) United States Patent
Finkelstein

(10) Patent No.: US 11,406,315 B2
(45) Date of Patent: Aug. 9, 2022

(54) PORTABLE SYSTEM AND METHOD FOR MONITORING BRAIN TRAUMA

(71) Applicant: Elliot Steven Finkelstein, Teaneck, NJ (US)

(72) Inventor: Elliot Steven Finkelstein, Teaneck, NJ (US)

(73) Assignee: Elliot Steven Finkelstein, Teaneck, NJ (US)

(*) Notice: Subject to any disclaimer, the term of this patent is extended or adjusted under 35 U.S.C. 154(b) by 417 days.

(21) Appl. No.: 16/467,065

(22) PCT Filed: Dec. 27, 2017

(86) PCT No.: PCT/IL2017/051393
§ 371 (c)(1),
(2) Date: Jun. 6, 2019

(87) PCT Pub. No.: WO2018/122847
PCT Pub. Date: Jul. 5, 2018

(65) Prior Publication Data
US 2019/0380612 A1    Dec. 19, 2019

Related U.S. Application Data

(60) Provisional application No. 62/439,916, filed on Dec. 29, 2016.

(51) Int. Cl.
*A61B 5/00* (2006.01)
*A61B 5/0205* (2006.01)
(Continued)

(52) U.S. Cl.
CPC ............ *A61B 5/369* (2021.01); *A61B 5/0205* (2013.01); *A61B 5/6803* (2013.01); *A61B 5/746* (2013.01);
(Continued)

(58) Field of Classification Search
CPC ......... A61B 5/369; A61B 5/746; A61B 5/024; A61B 5/6815; A61B 5/0205;
(Continued)

(56) References Cited

U.S. PATENT DOCUMENTS

| 3,978,856 A | 9/1976 | Michel |
| 4,610,259 A | 9/1986 | Cohen |

(Continued)

FOREIGN PATENT DOCUMENTS

WO    WO-2016110804 A1 *  7/2016  ........... A61B 5/0002

*Primary Examiner* — Christine H Matthews
*Assistant Examiner* — Joshua Daryl D Lannu

(57) ABSTRACT

A non-invasive system for monitoring brain trauma, the system comprising: a plurality of spaced apart brainwave sensors configured to monitor brainwaves of a user of the system; one or more force determination sensors, configured to determine an amount of force exerted on the user's head; and a processing unit configured to: obtain a plurality of brainwave readings from the brainwave sensors and a plurality of force readings from the force determination sensors; provide a notification upon the force readings indicating that the amount of force exerted on the user's head exceeds a threshold or upon the brainwave readings indicating an abnormal brain activity.

17 Claims, 3 Drawing Sheets

(51) Int. Cl.
*G01L 5/00* (2006.01)
*A61B 5/369* (2021.01)
*A61B 5/024* (2006.01)

(52) U.S. Cl.
CPC ............ *G01L 5/0052* (2013.01); *A61B 5/024* (2013.01); *A61B 5/4064* (2013.01); *A61B 5/6815* (2013.01); *A61B 5/6895* (2013.01)

(58) Field of Classification Search
CPC . A61B 5/4064; A61B 2503/10; A61B 5/6803; A61B 5/6895; G01L 5/0052; A42B 3/046; A42B 3/30
See application file for complete search history.

(56) References Cited

U.S. PATENT DOCUMENTS

| | | |
|---|---|---|
| 4,736,751 A | 4/1988 | Gevins |
| 7,904,144 B2 | 3/2011 | Causevic |
| 2002/0082514 A1 | 6/2002 | Williams |
| 2007/0255122 A1 | 11/2007 | Vol |
| 2009/0247894 A1 | 10/2009 | Causevic |
| 2012/0223833 A1 | 9/2012 | Thomas et al. |
| 2012/0289869 A1* | 11/2012 | Tyler .................... A61B 5/369 601/2 |
| 2014/0173812 A1* | 6/2014 | Krueger ............... A41D 13/015 2/455 |
| 2015/0230534 A1 | 8/2015 | McGuckin, Jr. |
| 2015/0285697 A1* | 10/2015 | O'Bier, II .............. A63B 71/00 2/411 |
| 2016/0100794 A1 | 4/2016 | Miller |
| 2016/0120432 A1 | 5/2016 | Sridhar |
| 2016/0213300 A1 | 7/2016 | Allen et al. |
| 2018/0116543 A1* | 5/2018 | Miller ................... G16H 20/00 |
| 2018/0303190 A1* | 10/2018 | Calilung .................. A42B 3/28 |
| 2020/0376288 A1* | 12/2020 | Smith ................... A61N 2/006 |

* cited by examiner

PORTABLE SYSTEM AND METHOD FOR MONITORING BRAIN TRAUMA

TECHNICAL FIELD

The invention relates to a portable system and method for monitoring brain trauma.

BACKGROUND

Mild Traumatic Brain Injury (MTBI) (also referred to as concussions, Mild Head Injury (MHI), minor head trauma, mild brain injury, etc.), are common and dangerous occurrences. In the United States alone about 1.74 million people sustain traumatic brain injury (TBI) each year. While most of these TBI cases are MTBIs, many more MTBI cases are not diagnosed and/or not reported. The two largest sources of these incidents are car accidents and falls. MTBI also frequently occurs in contact sports, with 1.6-3.8 million incidences resulting in multiple MTBIs per person. Soldiers are also susceptible to TBIs. Half the MTBI cases occur in patients between the ages of 15 and 34.

Subconcussive impacts can also be a cause for concern. These blows show no concussion symptoms, yet damage the brain. Changes to the brain caused by subconcussive forces are associated with the number of impacts. The brain damage caused by subconcussive forces was originally suspected to result in mild cognitive impairment. However, chronic depression and chronic traumatic encephalopathy (CTE) are also possible outcomes/conditions. The subconcussive impacts can cause significant changes in the white matter nerves. The limbic lobe and subcortical region of the brain are also changed.

There is thus a need in the art for a new method and system for monitoring brain trauma.

References considered to be relevant as background to the presently disclosed subject matter are listed below. Acknowledgement of the references herein is not to be inferred as meaning that these are in any way relevant to the patentability of the presently disclosed subject matter.

U.S. Pat. No. 7,904,144 (Causevic et al.), published on Mar. 8, 2011, discloses a method and apparatus for performing rapid brain assessment may provide emergency triage to head trauma patients by analyzing a combination of spontaneous and evoked brain potentials. The spontaneous and evoked potentials are analyzed, and the results classified, to present a real-time assessment of a patient's brain, diagnosing any potential abnormalities therein.

GENERAL DESCRIPTION

In accordance with a first aspect of the presently disclosed subject matter there is provided a non-invasive system for monitoring brain trauma, the system comprising: a plurality of spaced apart brainwave sensors configured to monitor brainwaves of a user of the system; one or more force determination sensors, configured to determine an amount of force exerted on the user's head; and a processing unit configured to: obtain a plurality of brainwave readings from the brainwave sensors and a plurality of force readings from the force determination sensors; and provide a notification upon the force readings indicating that the amount of force exerted on the user's head exceeds a threshold or upon the brainwave readings indicating an abnormal brain activity.

In some cases, the brainwave sensors and the force determination sensors are comprised within a head-worn device.

In some cases, the processing unit is comprised within the head-worn device.

In some cases, the processing unit is external to the head-worn device.

In some cases, the head-worn device is a helmet, having padding for attaching the brainwave sensors to corresponding locations on the user's head.

In some cases, the head-worn device is a headband attaching the brainwave sensors to corresponding locations on the user's head.

In some cases, the head-worn device includes at least one ear-worn device attachable to the user's ear.

In some cases, the system further comprises a heartbeat sensor configured to monitor heartbeats of the user and the processing resource is further configured to obtain a plurality of heartbeat readings from the heartbeat sensor and to provide the notification upon the heartbeat readings indicating a missing heartbeat.

In some cases, the processing unit is further configured to estimate an affected brain area utilizing the brainwave readings.

In some cases, the estimation is performed utilizing a magnitude and a time difference of a detected electrical echo in at least two of the brainwave readings obtained by at least two corresponding distinct brainwave sensors of the brainwave sensors.

In some cases, the notification includes an indication of the affected brain area.

In some cases, the brainwave sensors are passive sensors.

In some cases, the notification is provided to a second user, other than the user.

In accordance with a second aspect of the presently disclosed subject matter there is provided a method of monitoring brain trauma using a non-invasive system, the non-invasive system comprising: a plurality of spaced apart brainwave sensors configured to monitor brainwaves of a user of the system; one or more force determination sensors, configured to determine an amount of force exerted on the user's head; and a processing unit; the method comprising: obtaining a plurality of brainwave readings from the brainwave sensors and a plurality of force readings from the force determination sensors; and providing a notification upon the force readings indicating that the amount of force exerted on the user's head exceeds a threshold or upon the brainwave readings indicating an abnormal brain activity.

In some cases, the brainwave sensors and the force determination sensors are comprised within a head-worn device.

In some cases, the processing unit is comprised within the head-worn device.

In some cases, the processing unit is external to the head-worn device.

In some cases, the head-worn device is a helmet, having padding for attaching the brainwave sensors to corresponding locations on the user's head.

In some cases, the head-worn device is a headband attaching the brainwave sensors to corresponding locations on the user's head.

In some cases, the head-worn device includes at least one ear-worn device attachable to the user's ear.

In some cases, the non-invasive system further comprises a heartbeat sensor configured to monitor heartbeats of the user and wherein the method further comprises obtaining a plurality of heartbeat readings from the heartbeat sensor and providing the notification upon the heartbeat readings indicating a missing heartbeat.

In some cases, the method further comprises estimating an affected brain area utilizing the brainwave readings.

In some cases, the estimation is performed utilizing a magnitude and a time difference of a detected electrical echo in at least two of the brainwave readings obtained by at least two corresponding distinct brainwave sensors of the brainwave sensors.

In some cases, the notification includes an indication of the affected brain area.

In some cases, the brainwave sensors are passive sensors.

In some cases, the notification is provided to a second user, other than the user.

In accordance with a third aspect of the presently disclosed subject matter there is provided a non-transitory computer readable storage medium having computer readable program code embodied therewith, the computer readable program code executable by at least one processor of a non-invasive system to perform a method, the non-invasive system comprising a plurality of spaced-apart brainwave sensors configured to monitor brainwaves of a user of the system, and one or more force determination sensors, configured to determine an amount of force exerted on the user's head; the method comprising: obtaining a plurality of brainwave readings from the brainwave sensors and a plurality of force readings from the force determination sensors; providing a notification upon the force readings indicating that the amount of force exerted on the user's head exceeds a threshold or upon the brainwave readings indicating an abnormal brain activity.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which.

DETAILED DESCRIPTION

Figure 1:
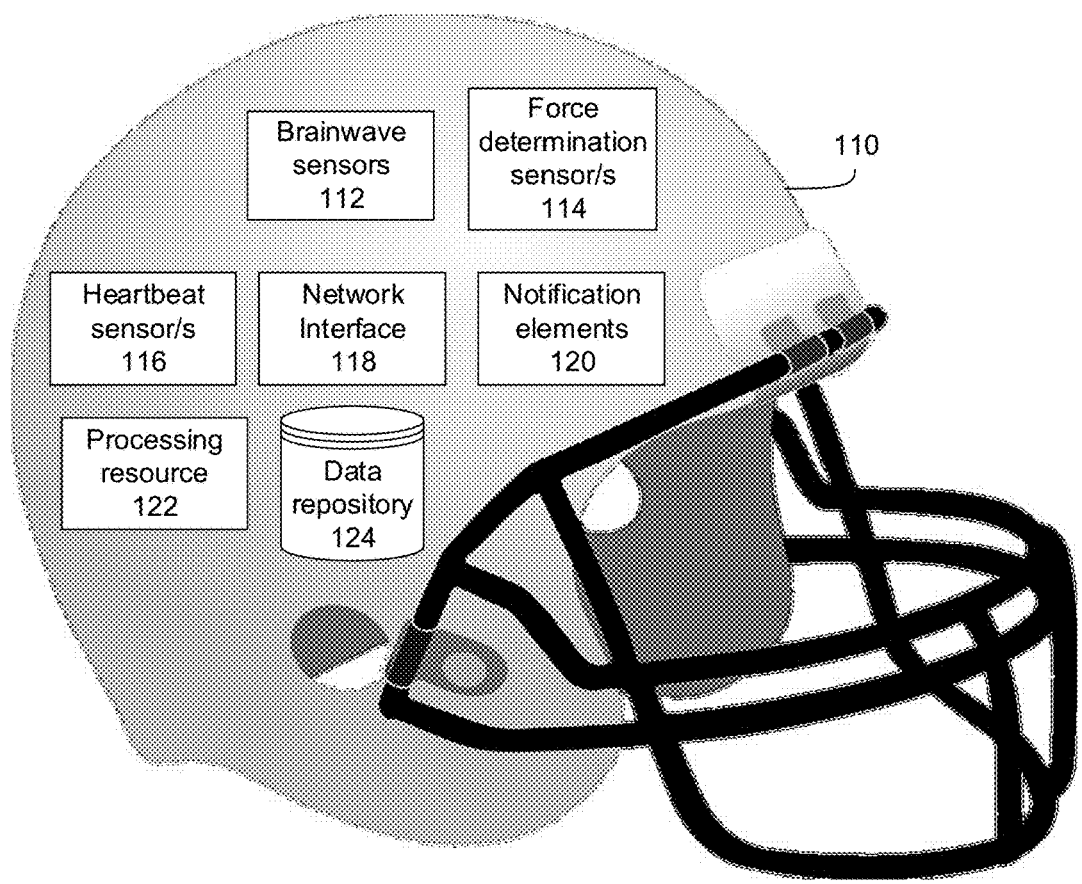
FIG. 1 is a schematic illustration of a head-worn device, in accordance with the presently disclosed subject matter.

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "obtaining", "providing", "estimating" or the like, include action and/or processes of a computer that manipulate and/or transform data into other data, said data represented as physical quantities, e.g. such as electronic quantities, and/or said data representing the physical objects. The terms "computer", "processor", and "controller" should be expansively construed to cover any kind of electronic device with data-processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

The operations in accordance with the teachings herein may be performed by a computer specially constructed for the desired purposes or by a general-purpose computer specially configured for the desired purpose by a computer program stored in a non-transitory computer readable storage medium. The term "non-transitory" is used herein to exclude transitory, propagating signals, but to otherwise include any volatile or non-volatile computer memory technology suitable to the application.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Figure 4:
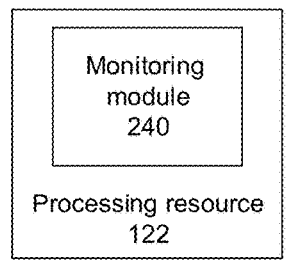
FIG. 4 is a block diagram schematically illustrating a processing resource, in accordance with the presently disclosed subject matter.
Figure 5:
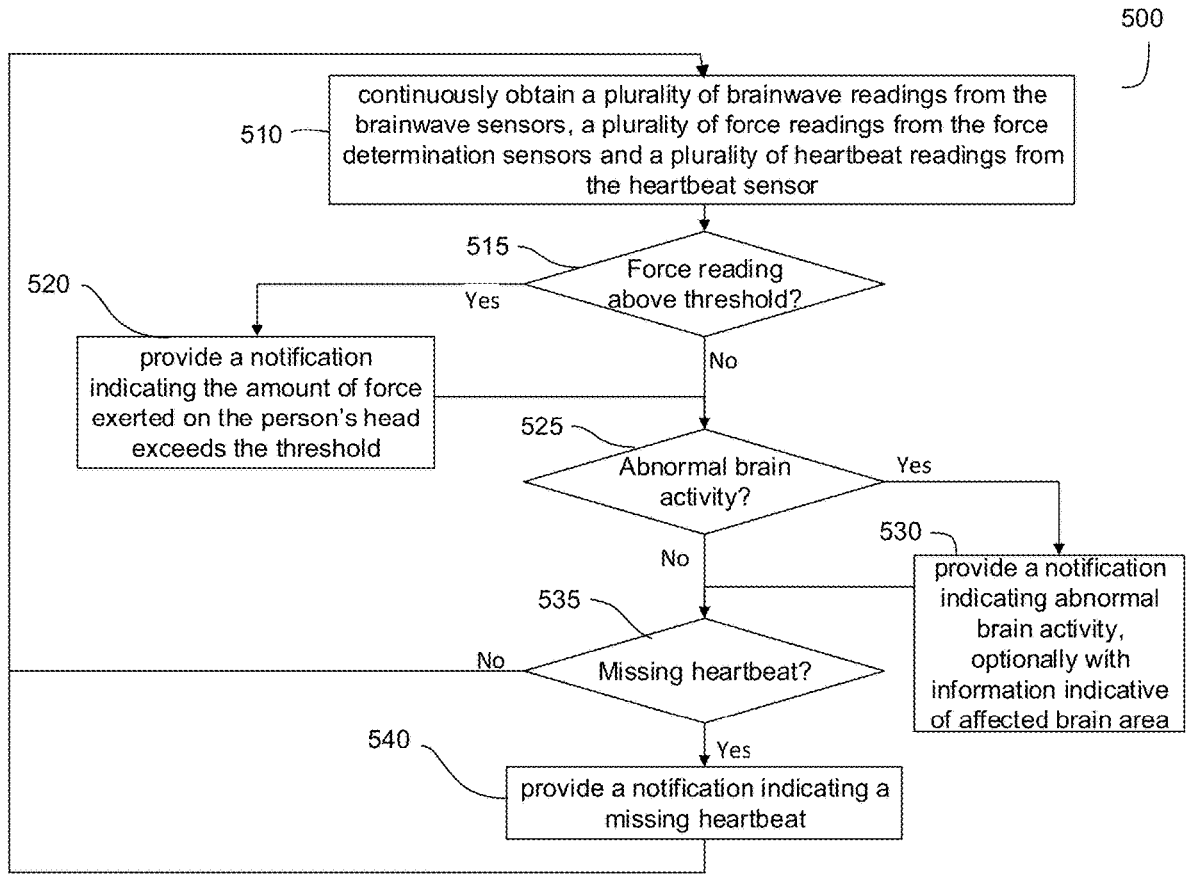
FIG. 5 is a flowchart illustrating one example of a sequence of operations carried out for monitoring brain trauma, in accordance with the presently disclosed subject matter.

In embodiments of the presently disclosed subject matter, fewer, more and/or different stages than those shown in FIG. 5 may be executed. In embodiments of the presently disclosed subject matter one or more stages illustrated in FIG. 5 may be executed in a different order and/or one or more groups of stages may be executed simultaneously. FIGS. 1-4 illustrate a general schematic of the system architecture in accordance with an embodiment of the presently disclosed subject matter. Each module in FIGS. 1-4 can be made up of any combination of software, hardware and/or firmware that performs the functions as defined and explained herein. The modules in FIGS. 1-4 may be centralized in one location or dispersed over more than one location. In other embodiments of the presently disclosed subject matter, the system may comprise fewer, more, and/or different modules than those shown in FIGS. 1-4.

Bearing this in mind, attention is drawn to FIG. 1, showing a schematic illustration of a head-worn device, in accordance with the presently disclosed subject matter.

According to certain examples of the presently disclosed subject matter, a head-worn device 110, such as the helmet shown in the illustration, or a headband, or any other head-worn device, including devices worn on and/or inside the ears of the person wearing the device (for the sake of clarity—the term "head-worn device" according to the presently disclosed subject matter is to be construed as including also ear-worn device/s attachable to an ear/s), is provided. The head-worn device 110 comprises a plurality of spaced apart brainwave sensors 112 configured to monitor brainwaves of a person wearing the head-worn device 110. The brainwave sensors 112 can be, for example, passive sensors, such as Electroencephalography (EEG) electrodes, or other types of sensors. In some cases, the brainwave sensors 112 can be active sensors such as ones used in Near Infrared Spectroscopy (NIRS). The brainwave sensors 112 can be positioned so that in the contact points thereof with the head of the person wearing the head-worn device 110 there is no hair, or the hair is low-cut, as in some cases the less hair there is the better the reading quality is expected to be. Such points can be, for example, the forehead, the neck, near the ears, on the temples (located on the side of the head, behind the eyes). In a particular example, a first brainwave sensor 112 and a second brainwave sensor 112 are positioned so that one contacts the top of the forehead of the person wearing the head-worn device 110 above the left eye and the other contacts the top of the forehead of the person wearing the head-worn device 110 above the right eye; a third brainwave sensor 112 is positioned so that it contacts a spot between the left ear and the left sideburn of the person wearing the head-worn device 110; a fourth brainwave sensor 112 is positioned so that it contacts a spot between the right ear and the right sideburn of the person wearing the head-worn device 110; a fifth brainwave sensor 112 and a sixth brainwave sensor 112 are positioned so that they contact the left and right sides of the back of the neck of the person wearing the head-worn device 110 respectively, and a seventh brainwave sensor 112 and eighth brainwave sensor 112 are positioned so that they contact the left and right temples of the person wearing the head-worn device 110 respectively. It is to be noted that this is merely one example and the brainwave sensors 112 can be positioned in other manners, mutatis mutandis. It is to be further noted that in order for the brainwave sensors 112 to be pressed against the contact points on the head of the person wearing the head-worn device 110, padding can be placed in an appropriate manner inside the head-worn device 110, while making sure that it does not interfere with the operation of the various sensors. In some cases, the padding can also be used to cushion various impacts.

It is to be noted that in some cases the readings obtained by the brainwave sensors 112 are used in their raw form, and such readings are used to detect regional abnormalities, as detailed herein. Identifying regional abnormalities can enable locating an affected brain area, as detailed herein, inter alia with respect to FIG. 5. In other cases, various statistical tools can be used to analyze the raw signals for improved interpretation. The head-worn device 110 further comprises one or more force determination sensors 114, configured to determine an amount of force exerted on the head of the person wearing the head-worn device 110. The force determination sensors 114 can be Force Sensing Resistors (FSRs), Piezoelectric sensors, accelerometer, any other sensor capable of obtaining information that enables determining a force exerted on the head of the person wearing the head-worn device 110, or any combination of two or more of those sensor types. In a particular example, a first and a second force determination sensors 114 are positioned so that they contact substantially the center of the left and right hemispheres on the top of the head of the person wearing the head-worn device 110, a third force determination sensor 114 is positioned so that it contacts substantially the middle of the forehead of the person wearing the head-worn device 110, a fourth force determination sensor 114 is positioned so that it contacts substantially the middle of the back of the head of the person wearing the head-worn device 110, a fifth and sixth force determination sensors 114 are positioned so that they contact substantially the middle of the left and right sides of the head of the person wearing the head-worn device 110 respectively, and four additional force determination sensors 114 are positioned so that they contact the front-right, front-left back-right and back-left corners of the head of the person wearing the head-worn device 110 respectively. It is to be noted that this is merely one example and the force determination sensors 114 can be positioned in other manners, mutatis mutandis.

In some cases, the head-worn device 110 further comprises one or more heartbeat sensors 116 configured to monitor heartbeats of the person wearing the head-worn device 110. The heartbeat sensors 116 can be located on areas where the blood vessels are close to the surface, such as the ears. In a particular example, a heartbeat sensor 116 can be attached to, or tightly pressed against, an ear of the person wearing the head-worn device 110, and optionally a second heartbeat sensor 116 can be attached to, or tightly pressed against, the other ear of the person wearing the head-worn device 110. It is to be noted that this is merely one example and the heartbeat sensors 116 can be positioned in other manners, mutatis mutandis. It is to be further noted that in some cases, the heartbeat sensors 116 can use out of skin technology such as flow monitoring using light or the change in pressure/signals due to the flow of blood in a place like the ears, etc.

The head-worn device 110 can optionally also comprise one or more notification elements 120, that can enable providing notifications to the person wearing the head-worn device 110, as further detailed herein, inter alia with reference to FIG. 5. In some cases, the notification elements 120 can be vibrating elements and/or speakers and/or lights and/or any other device that can generate a notification that can be sensed by the person wearing the head-worn device 110.

In some cases, all or part of the processing in accordance with the presently disclosed subject matter can be performed by the head-worn device 110, that can optionally be a standalone unit, having data storage and processing capabilities. In such cases, the head-worn device 110 can further comprise a data repository 124 and a processing resource 122.

The processing resource 122 can be one or more processing units (e.g. central processing units), microprocessors, microcontrollers (e.g. microcontroller units (MCUs)) or any other computing devices or modules, including multiple and/or parallel and/or distributed processing units, which are adapted to independently or cooperatively process data for controlling relevant head-worn device 110 resources and for enabling operations related to head-worn device 110 resources, as further detailed with respect to FIG. 4.

The data repository 124 (e.g. a database, a storage system, a memory including Read Only Memory—ROM, Random Access Memory—RAM, or any other type of memory, etc.) can be configured to store data, including, inter alia, information of readings obtained by the sensors and/or predetermined or dynamically calculated thresholds to be compared with such readings, etc. In some cases, data repository 124 can be further configured to enable retrieval and/or update and/or deletion of the stored data. It is to be noted that in some cases, data repository 124 can be distributed (for example, part of the data repository can be local (i.e. inside the head worn device), and another part can thereof be external (e.g. within the external processing system 140)).

Alternatively, or additionally, all or part of the data storage and/or processing can be performed externally to the head-worn device 110, or the notifications can be provided using output means external to the head-worn device. In such cases, the head-worn device 110 can further include a network interface 118. Network interface 118 can enable wirelessly connecting the head-worn device 110 to the communication network 130 and can enable it to send and receive data sent thereto through the communication network 130, including sending readings from the various sensors (the brainwave sensors 112, the force determination sensors 114, the heartbeat sensors 116) to an external processing system 140, sending commands for operating external output means to provide various notifications, etc., as further detailed herein, inter alia with reference to FIG. 5.

Although a helmet is shown in the illustration, other head-worn devices, such as a headband, or other types of head worn devices, can be used, mutatis mutandis.

Figure 2:
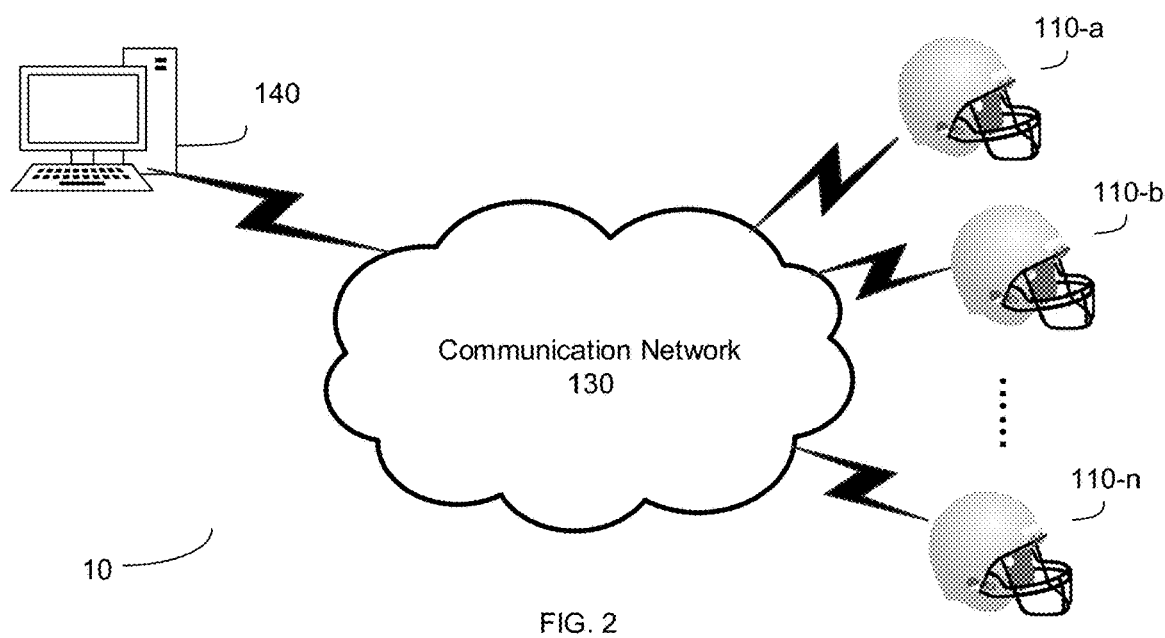
FIG. 2 is a schematic illustration of a system including a plurality of head-worn devices, in accordance with the presently disclosed subject matter.

Turning to FIG. 2, there is shown a schematic illustration of a system including a plurality of head-worn devices, in accordance with the presently disclosed subject matter.

According to certain examples of the presently disclosed subject matter, there is provided a system 10 comprising a plurality of head-worn devices (shown in the illustration as 110-*a*, 110-*b*, . . . , 110-*n*). Each of the head-worn devices (110-*a*, . . . , 110-*n*) is a head-worn device in accordance with the teachings of the above description of FIG. 1. Such system 10, comprising a plurality of head-worn devices (110-*a*, . . . , 110-*n*) can be used for example by sports teams, such as Football (also known as American Football or gridiron) teams, where each player wears a head-worn device 110. In such case, it is desirable to monitor each player playing on a playing field for identifying brain trauma that can be caused for example by being hit by another player, or by falling on the ground, etc.

The plurality of head-worn devices 110-*a*, . . . , 110-*n* can be connected to a communication network 130, through which the data collected by the plurality of sensors (including the brainwave sensors 112 and/or the force determination sensors 114 and/or the heartbeat sensors 116) can be sent to an external processing system 140, for data storage and processing as further detailed herein, inter alia with reference to FIG. 5.

Figure 3:
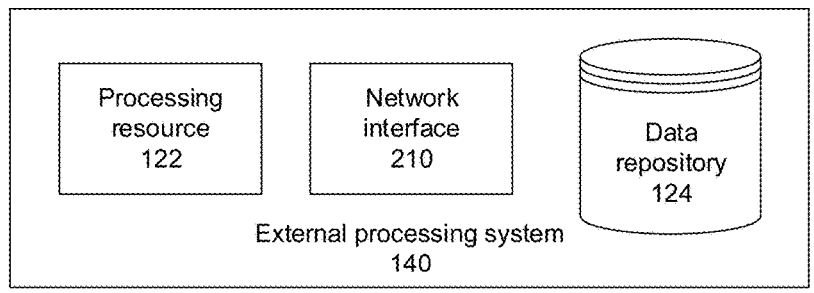
FIG. 3 is a block diagram schematically illustrating an external processing system, in accordance with the presently disclosed subject matter.

Attention is drawn to FIG. 3 showing a block diagram schematically illustrating an external processing system, in accordance with the presently disclosed subject matter.

As indicated herein, in some cases all or part of the data storage and/or processing in accordance with the presently disclosed subject matter is performed externally to the head-worn device 110, e.g. on an external processing system 140. In such cases, the external processing system 140 can comprise a network interface 210. Network interface 210 can enable wirelessly connecting the external processing system 140 to communication network 130 and can enable it to send and receive data sent thereto through the communication network 130, including receiving readings from the various sensors (the brainwave sensors 112, the force determination sensors 114, the heartbeat sensors 116) of the head-worn devices (110-*a*, . . . , 110-*n*), etc., as further detailed herein, inter alia with reference to FIG. 5.

The external processing system 140 can further comprise a processing resource 122 and/or a data repository 124. The processing resource 122 can be one or more processing units (e.g. central processing units), microprocessors, microcontrollers (e.g. microcontroller units (MCUs)) or any other computing devices or modules, including multiple and/or parallel and/or distributed processing units, which are adapted to independently or cooperatively process data for controlling relevant external processing system 140 resources and for enabling operations related to external processing system 140 resources, as further detailed with respect to FIG. 4.

The data repository 124 (e.g. a database, a storage system, a memory including Read Only Memory—ROM, Random Access Memory—RAM, or any other type of memory, etc.) can be configured to store data, including, inter alia, information of readings obtained by the sensors and/or predetermined or dynamically calculated thresholds to be compared with such readings, etc. In some cases, data repository 124 can be further configured to enable retrieval and/or update and/or deletion of the stored data. It is to be noted that in some cases, data repository 124 can be distributed.

FIG. 4 is a block diagram schematically illustrating a processing resource, in accordance with the presently disclosed subject matter.

The processing in accordance with the presently disclosed subject matter can be performed by a processing resource 122 comprised within one or more of the head-worn devices (110-*a* to 110-*n*), or within an external processing system 140. In some cases, the processing can be performed by a plurality of processing resources 122 that can be optionally distributed between one or more head-worn devices 110 and/or one or more external processing systems 140. Irrespectively, the processing resource 122 can comprise a monitoring module 240. The monitoring module 240 can be configured to monitor brain trauma of one or more persons wearing one or more respective head-worn devices 110. In this respect, attention is drawn to FIG. 5 where a flowchart illustrating one example of a sequence of operations carried out for monitoring brain trauma, in accordance with the presently disclosed subject matter, is shown.

According to some examples of the presently disclosed subject matter, processing resource 122 (that, as indicated herein, can be comprised within one or more of the head-worn devices (110-*a* to 110-*n*), and/or within an external processing system 140) can be configured to perform a monitoring process 500, e.g. utilizing the monitoring module 240.

For this purpose, processing resource 122 can be configured to continuously obtain, from each of the one or more head-worn devices (e.g. head-worn devices 110-*a* to 110-*n*), a plurality of brainwave readings from the corresponding brainwave sensors 112, a plurality of force readings from the force determination sensors 114 and optionally a plurality of heartbeat readings from the heartbeat sensor/s 116 (block 510).

The processing resource 122 can be further configured to check if any of the force readings obtained from each head-worn device 110 exceed a pre-defined threshold (block 515), and if so—provide a notification indicating that the amount of force exerted on the head of the person wearing the corresponding head-worn device 110 exceeded the pre-determined threshold (block 520).

In some cases, the threshold can be set as 20 g/30 g/35 g or any other pre-determined force. In this respect, it is noted that current research shows that a force of 30 g is likely to cause a concussion.

Additionally, or alternatively, the threshold can be set to be a pre-determined number of blows, during a given time window (e.g. during a single American Football game, during a single quarter of an American Football game, during five minutes, etc.), each exceeding a second threshold that can be set as 5 g/10 g/15 g. In this respect, research shows that repeated blows of 10 g or more can cause brain damage.

The notification can be provided to the person wearing the corresponding head-worn device 110, e.g. utilizing the notification elements 120. Additionally, or alternatively, the notification can be provided to another user, such as a coach of the sports team or any other person in charge of monitoring the medical condition of the players wearing the head-worn devices (110-a to 110-n), e.g. via an output mechanism such as a display (including, for example, a display of a smartphone, e.g. by sending a text message to the user), speakers, vibrating elements, or any other output device accessible to such user.

Figure 6:
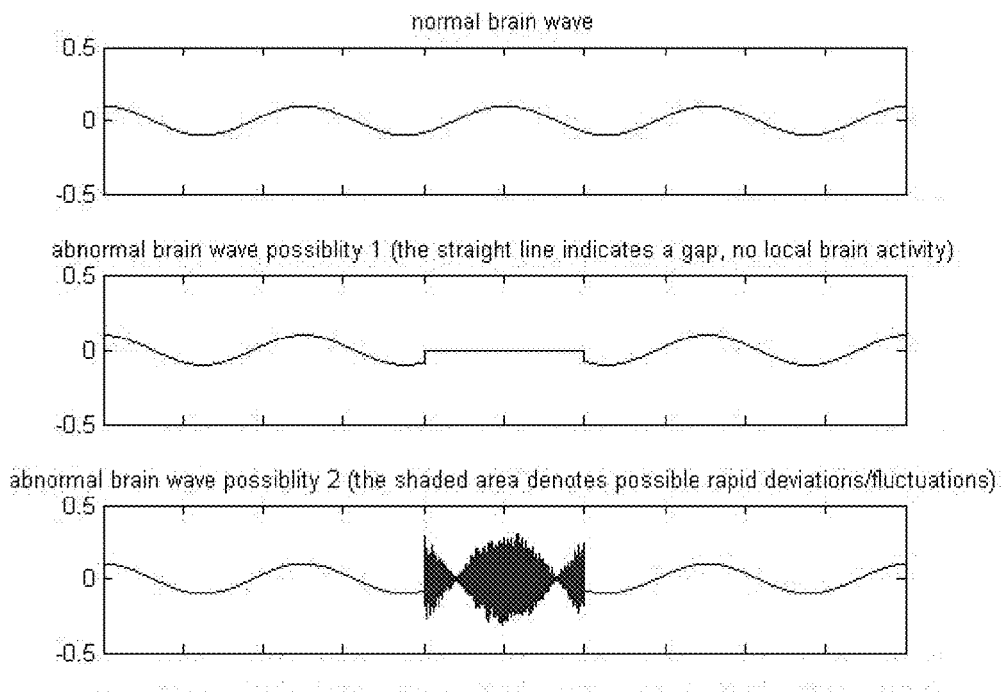
FIG. 6 is an exemplary illustration of normal brain wave vs. abnormal brain waves.

If the pre-defined threshold is not exceeded at block 515, or after providing the notification at block 520, the processing resource 122 can check if any of the brainwave readings obtained from each head-worn device 110 indicate an abnormal brain activity (block 525). An abnormal brain activity can be indicative of brain trauma. For this purpose, the brainwave readings can be compared with information indicative of normal readings. The information indicative of normal readings can be generic (i.e. not specific to the person wearing the corresponding head-worn device 110), or personalized (i.e. specific to the person wearing the corresponding head-worn device 110). If the brainwave readings are indicative of abnormal brain activity (e.g. deviating from the normal EEG form, for example as shown in FIG. 6, which illustrates a normal brainwave in the top graph vs. two exemplary types of abnormal brain activity in the middle and bottom graphs), the processing resource 122 can be configured to provide a notification indicating that the brain activity of the person wearing the corresponding head-worn device 110 is abnormal (block 530). The notification can be provided to the person wearing the corresponding head-worn device 110, e.g. utilizing the notification elements 120. Additionally, or alternatively, the notification can be provided to another user, such as a coach of the sports team or any other person in charge of monitoring the medical condition of the players wearing the head-worn devices (110-a to 110-n), e.g. via an output mechanism such as a display (including, for example, a display of a smartphone, e.g. by sending a text message to the user), speakers, vibrating elements, or any other output device accessible to such user.

In some cases, the processing resource 122 can be further configured to estimate an affected brain area of the person wearing the corresponding head-worn device 110. Such estimation can be performed utilizing a magnitude and a time difference between the force determination sensors 114 detecting a force and the brainwave sensors 112 detecting abnormal brain activity.

Figure 7:
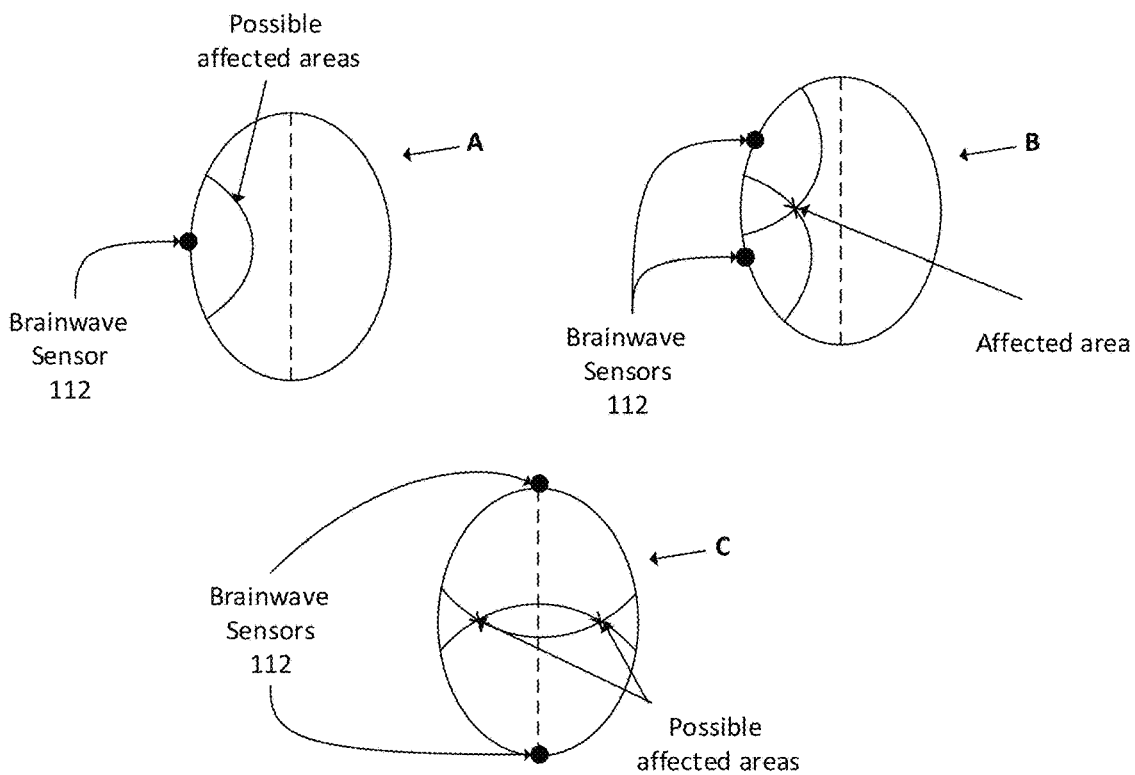
FIG. 7 is an illustration of three examples of estimating an affected brain area, in accordance with the presently disclosed subject matter.

Attention is drawn, in this regard, to FIG. 7, showing three examples of estimating an affected brain area, in accordance with the presently disclosed subject matter. In the first example, marked "A", a single brainwave sensor 112 picks up an abnormal brain activity. Utilizing the time difference between the time at which the force determination sensors 114 detected a force, and the time at which the brainwave sensor 112 picked up the abnormal brain activity, the distance of the affected brain area can be estimated. In the illustrated example, the estimated affected brain area is shown by the arc marked "possible locations". In the second example, marked "B", two brainwave sensors 112 pick up abnormal brain activity, each at a certain corresponding point in time. Utilizing the time difference between the time at which the force determination sensors 114 detected a force, and the time at which each of the brainwave sensors 112 picked up the abnormal brain activity, the distance of the affected brain area from each sensor can be estimated, and the intersection point of the arcs representing the calculated distance from each brainwave sensor 112—is the estimated affected brain area. In the example marked "B", both brainwave sensors are placed on the same side of the head of the person wearing the head-worn device. The example marked "C" shows a scenario at which the brainwave sensors that pick up the abnormal brain activity are located at opposite sides of the head. In such scenario, there are two intersection points between the arcs representing the calculated distances from the corresponding brainwave sensors 112, both of which are possible affected brain areas. It can be appreciated that having information from more than two brainwave sensors 112 can enable a more accurate estimation of the affected brain area, and having at least three brainwave sensors 112 can enable a three-dimensional estimation.

Returning to FIG. 5, in some cases, when the processing resource 122 can obtain heartbeat readings (e.g. in cases where at least one head-worn device 110 comprises one or more heartbeat sensors 116), the processing resource 122 can be further configured to check for missing heartbeats (block 535). In some cases, when a person is hit, it may result in the heart missing a beat. Missing a heartbeat is indicative of brain trauma or another serious condition. If a missing heartbeat is identified, the processing resource 122 can be configured to provide a notification indicating that the heart of the person wearing the corresponding head-worn device 110 missed a beat (block 530). The notification can be provided to the person wearing the corresponding head-worn device 110, e.g. utilizing the notification elements 120. Additionally, or alternatively, the notification can be provided to another user, such as a coach of the sports team or any other person in charge of monitoring the medical condition of the players wearing the head-worn devices (110-a to 110-n), e.g. via an output mechanism such as a display (including, for example, a display of a smartphone, e.g. by sending a text message to the user), speakers, vibrating elements, or any other output device accessible to such user.

It is to be noted that, with reference to FIG. 5, some of the blocks can be integrated into a consolidated block or can be broken down to a few blocks and/or other blocks may be added. Furthermore, in some cases, the blocks can be performed in a different order than described herein (for example, blocks 525 and 530 can be performed before blocks 515 and 520, blocks 535 and 540 can be performed before blocks 525 and 530, etc.). It is to be further noted that some of the blocks are optional. It should be also noted that whilst the flow diagram is described also with reference to the system elements that realizes them, this is by no means binding, and the blocks can be performed by elements other than those described herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

What is claimed is:

1. A non-invasive system for monitoring brain trauma, the system comprising:
   a plurality of spaced apart brainwave sensors configured to monitor brainwaves of a user of the system;
   one or more force determination sensors, configured to determine an amount of force exerted on the user's head; and
   a processing resource configured to:
   obtain a plurality of brainwave readings from the brainwave sensors and a plurality of force readings from the one or more force determination sensors;
   determine (a) that any of the plurality of force readings indicate that the amount of force exerted on the user's head at a given time exceeds a threshold, and (b) that any of the plurality of brainwave readings indicate abnormal brain activity resulting from the force exerted on the user's head at the given time;
   estimate an affected brain area of the user utilizing a time difference between the given time and times at which each of the brainwave readings indicating abnormal brain activity resulting from the force exerted on the user's head at the given time was obtained by the respective brainwave sensors; and
   provide a notification including an indication of the affected brain area.

2. The non-invasive system of claim 1, wherein the brainwave sensors and the one or more force determination sensors are comprised within a device configured to be worn on the user's head.

3. The non-invasive system of claim 2, wherein the device is a helmet, having padding for attaching the brainwave sensors to corresponding locations on the user's head.

4. The non-invasive system of claim 2, wherein the device is a headband attaching the brainwave sensors to corresponding locations on the user's head.

5. The non-invasive system of claim 2, wherein the device includes at least one ear-worn device attachable to the user's ear.

6. The non-invasive system of claim 1, further comprising a heartbeat sensor configured to monitor heartbeats of the user and wherein the processing resource is further configured to obtain a plurality of heartbeat readings from the heartbeat sensor and to provide the notification upon the heartbeat readings indicating a missing heartbeat.

7. The non-invasive system of claim 1, wherein the brainwave sensors are passive sensors.

8. The non-invasive system of claim 1, wherein the notification is provided to a second user, other than the user.

9. A method of monitoring brain trauma using a non-invasive system, the non-invasive system comprising:
   a plurality of spaced apart brainwave sensors configured to monitor brainwaves of a user of the system;
   one or more force determination sensors, configured to determine an amount of force exerted on the user's head; and
   a processing resource;
   the method comprising:
   obtaining, by the processing resource, a plurality of brainwave readings from the brainwave sensors and a plurality of force readings from the one or more force determination sensors;
   determining, by the processing resource, (a) that any of the plurality of force readings indicate that the amount of force exerted on the user's head at a given time exceeds a threshold, and (b) that any of the plurality of brainwave readings indicate abnormal brain activity resulting from the force exerted on the user's head at the given time;
   estimating an affected brain area of the user utilizing a time difference between the given time and times at which each of the brainwave readings indicating abnormal brain activity resulting from the force exerted on the user's head at the given time was obtained by the respective brainwave sensors; and
   providing, by the processing resource, a notification including an indication of the affected brain area.

10. The method of claim 9, wherein the brainwave sensors and the one or more force determination sensors are comprised within a device configured to be worn on the user's head.

11. The method of claim 10 wherein the device is a helmet having padding for attaching the sensors to corresponding locations on the user's head.

12. The method of claim 10, wherein the device is a headband attaching the brainwave sensors to corresponding locations on the user's head.

13. The method of claim 10, wherein the device includes at least one ear-worn device attachable to the user's ear.

14. The method of claim 9, wherein the non-invasive system further comprises a heartbeat sensor configured to monitor heartbeats of the user and wherein the method further comprises obtaining a plurality of heartbeat readings from the heartbeat sensor and providing the notification upon the heartbeat readings indicating a missing heartbeat.

15. The method of claim 9, wherein the brainwave sensors are passive sensors.

16. The method of claim 9, wherein the notification is provided to a second user, other than the user.

17. A non-transitory computer readable storage medium having computer readable program code embodied therein, the computer readable program code executable by at least one processor of a non-invasive system to perform a method, the non-invasive system comprising a plurality of spaced apart brainwave sensors configured to monitor brainwaves of a user of the system, and one or more force determination sensors, configured to determine an amount of force exerted on the user's head, the method comprising:
   obtaining, by the processing resource, a plurality of brainwave readings from the brainwave sensors and a plurality of force readings from the one or more force determination sensors;
   determining, by the processing resource, (a) that any of the plurality of force readings indicate that the amount of force exerted on the user's head at a given time exceeds a threshold, and (b) that any of the plurality of brainwave readings indicate abnormal brain activity resulting from the force exerted on the user's head at the given time;

estimating an affected brain area of the user utilizing a time difference between the given time and times at which each of the brainwave readings indicating abnormal brain activity resulting from the force exerted on the user's head at the given time was obtained by the respective brainwave sensors; and providing, by the processing resource, a notification including an indication of the affected brain area.

* * * * *